United States Patent
Fontanarosa

(10) Patent No.: US 10,974,073 B2
(45) Date of Patent: Apr. 13, 2021

(54) ULTRASONIC IMAGE GUIDANCE OF RADIATION THERAPY PROCEDURES

(71) Applicant: KONINKLIJKE PHILIPS N.V., Eindhoven (NL)

(72) Inventor: Davide Fontanarosa, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 673 days.

(21) Appl. No.: 15/514,906

(22) PCT Filed: Sep. 28, 2015

(86) PCT No.: PCT/EP2015/072290
§ 371 (c)(1),
(2) Date: Mar. 28, 2017

(87) PCT Pub. No.: WO2016/050709
PCT Pub. Date: Apr. 7, 2016

(65) Prior Publication Data
US 2018/0229057 A1    Aug. 16, 2018

(30) Foreign Application Priority Data
Sep. 30, 2014   (EP) .................................... 14187003

(51) Int. Cl.
*A61N 5/10*    (2006.01)
*A61B 8/08*    (2006.01)
*A61B 8/00*    (2006.01)

(52) U.S. Cl.
CPC ............ *A61N 5/1049* (2013.01); *A61B 8/085* (2013.01); *A61B 8/4227* (2013.01);
(Continued)

(58) Field of Classification Search
CPC ................ A61N 5/1049; A61N 5/1067; A61N 2005/1058; A61B 8/4455; A61B 8/4236;
(Continued)

(56) References Cited

U.S. PATENT DOCUMENTS

| 5,997,479 A | 12/1999 | Savord |
| 6,019,724 A | 2/2000 | Gronningsaeter et al. |

(Continued)

FOREIGN PATENT DOCUMENTS

| EP | 2358276 A1 | 8/2011 |
| JP | 2008538716 A | 11/2008 |

(Continued)

OTHER PUBLICATIONS

Langen et al "Evaluation of Ultrasound Based Prostate Localization for Image Guided Radiotherapy" Int. J. Radiat. Oncol. Biol. Physics, vol. 57 (2003) p. 635-644.

(Continued)

*Primary Examiner* — Sanjay Cattungal

(57) ABSTRACT

An ultrasonic diagnostic imaging system has a thin two dimensional array transducer probe which is taped or belted to a patient to image a target region during radiotherapy. The radiotherapy procedure is conducted based upon planning done based on images of the target region acquired prior to the procedure. The array transducer is operated by an ultrasound system to produce three dimensional images of the target region by electronic beam steering, either during or between fractions of the treatment procedure. The ultrasound images are used to adjust the treatment plan in response to any movement or displacement of the target anatomy during the treatment procedure.

11 Claims, 3 Drawing Sheets

(52) U.S. Cl.
CPC .......... *A61B 8/4236* (2013.01); *A61B 8/4455* (2013.01); *A61N 5/1067* (2013.01); *A61B 8/483* (2013.01); *A61B 8/582* (2013.01); *A61N 2005/1058* (2013.01)

(58) Field of Classification Search
CPC ....... A61B 8/4227; A61B 8/085; A61B 8/483; A61B 8/582
See application file for complete search history.

(56) References Cited

U.S. PATENT DOCUMENTS

| | | | |
|---|---|---|---|
| 6,436,048 B1 | 8/2002 | Pesque | |
| 8,348,846 B2* | 1/2013 | Gunther | A61B 8/08 600/437 |
| 2002/0045820 A1* | 4/2002 | Pesque | A61B 8/06 600/443 |
| 2009/0076379 A1* | 3/2009 | Hamill | A61B 8/4245 600/424 |
| 2009/0216121 A1* | 8/2009 | Lacoste | A61N 7/02 600/439 |
| 2009/0306502 A1* | 12/2009 | Lacoste | A61B 8/4281 600/439 |
| 2011/0009742 A1* | 1/2011 | Lachaine | A61B 8/4227 600/427 |
| 2011/0201934 A1* | 8/2011 | Robinson | G01S 7/5208 600/443 |
| 2013/0237822 A1 | 9/2013 | Gross et al. | |
| 2014/0163374 A1* | 6/2014 | Ogasawara | A61B 8/4236 600/443 |

FOREIGN PATENT DOCUMENTS

| | | |
|---|---|---|
| JP | 2013078570 A | 5/2013 |
| JP | 2014100590 A | 6/2014 |
| WO | 2006114735 A1 | 11/2006 |

OTHER PUBLICATIONS

Van Den Heuvel et al "Independent Verification of Ultrasound Based Image Guided Radiation Treatment . . . " Med. Phys. vol. 30, (2003) p. 2878-87.

Abramowitz et al "Noninvasive Real-Time Prostate Tracking Using a Transperineal Ultrasound Approach" In'l J. Rad. Oncol. Biol & Physics, vol. 84 (2012) p. S133.

Court et al "Automatic Online Adaptive Radiation Therapy Techniques for Targets With Significant Shape Change" Phys. Med. Biol. vol. 51 (2006) pp. 2493-2450.

Artignan X, Smitsmans M H, Lebesque J V, Jaffray D A, van Her M and Bartelink H "Online ultrasound image guidance for radiotherapy of prostate cancer: impact of image acquisition on prostate displacement" Int J Radiat Oncol Biol Phys 59 595-601(2004).

Barett S B, Ter Haar G R, Ziskin M C, Roti H D, Duck F A and Maeda K "International recommendations and guidelines for the safe use of diagnostic ultrasound in medicine" Ultrasound Med Biol 26 355-66 (2002).

Brascho D J "Tumor localization and treatment planning with ultrasound" Cancer 39 697-705 (1997).

Dietz H P 2004 Ultrasound imaging of the pelvic floor. Part II: three-dimensional or volume imaging Ultrasound Obstet Gynecol 23 615-25.

Enke C, Ayyangar K, Saw C B, Zhen W, Thompson R B and Raman N V "Inter-observer variation in prostate localization utilizing BAT" International journal of radiation oncology, biology, physics 54 269 (2002).

Evans P M Anatomical imaging for radiotherapy Phys Med Biol 53 R151-R91 (2008).

Fontanarosa D, van der Meer S, Harris E and Verhaegen F "A CT based correction method for speed of sound aberration for ultrasound based image guided radiotherapy" Med Phys 38 2665-73 (2011).

Fuchsjager M H, Maier A G, Schima W, Zebedin E, Herbst F, Mittlbock M, Wrba F and Lechner G L "Comparison of transrectal sonography and double-contrast MR imaging when staging rectal cancer" AJR Am J Roentgenol 181 421-7 (2003).

Harris E J, Donovan E M, Coles C E, de Boer H C, Poynter A, Rawlings C, Wishart G C and Evans P M 2012 How does imaging frequency and soft tissue motion affect the PTV margin size in partial breast and boost radiotherapy? Radiother Oncol 103 166-71.

Lattanzi J, McNeeley S, Pinover W, Horwitz E, Das I, Schultheiss T E and Hanks G E 1999 A comparison of daily CT localization to a daily ultrasound-based system in prostate cancer International journal of radiation oncology, biology, physics 43 719-25.

Majida M, Braekken I H, Umek W, Bo K, Saltyte Benth J and Ellstrom Engh M 2009 Interobserver repeatability of three- and four-dimensional transperineal ultrasound assessment of pelvic floor muscle anatomy and function Ultrasound Obstet Gynecol 33 567-73.

Rose R J and S.Allwin 2013 Computerized Cancer Detection and Classification Using Ultrasound Images: A Survey International Journal of Engineering Research and Development 5 36-47.

Uematsu M, Fukui T, Shioda A, Tokumitsu H, Takai K, Kojima T, Asai Y and Kusano S 1996 A dual computed tomography linear accelerator unit for stereotactic radiation therapy: a new approach without cranially fixated stereotactic frames Int J Radiat Oncol Biol Phys 35 587-92.

* cited by examiner

ULTRASONIC IMAGE GUIDANCE OF RADIATION THERAPY PROCEDURES

This application is the U.S. National Phase application under 35 U.S.C. § 371 of International Application No. PCT/EP2015/072290, filed on Sep. 28, 2015, which claims the benefit of EP Application Ser. No. 14187003.0 filed Sep. 30, 2014. These applications are hereby incorporated by reference herein.

FIELD OF THE INVENTION

This invention relates to radiation therapy procedures and, in particular, to the use of ultrasonic imaging to guide such procedures.

BACKGROUND OF THE INVENTION

In preparation for radiation therapy or radiotherapy, medical diagnostic images are taken of the treatment target (tumor) to plan the procedure. Both the location (depth) of the tumor and the presence of surrounding healthy tissue structures are taken into consideration in planning the procedure. These considerations lead to a choice of the intensity and focus of the radiation dose, the locations in the tumor where treatment fractions are to be delivered, and the path of the radiation beam through surrounding healthy tissue. Typically the planning images are CT images of the target region, called a simulation CT scan. Based on the CT images, the outcome of the planning is a set of instructions that are sent to the treatment d delivery device, usually a linear accelerator. The instructions define the path of radiation delivery and the planned dose distribution inside the patient. Since the planning images are acquired prior to commencement of the treatment, it is of paramount importance that the treatment target (the tumor) and the surrounding structures (healthy tissues) are positioned exactly as they appear in the simulation CT scan before each treatment fraction; otherwise the dose will not be safely and correctly delivered. Patient positioning is therefore becoming increasingly of interest in order to obtain the desired results of treatment.

One of the modalities which can be used in image guidance of radiotherapy is ultrasound imaging, which has some unique characteristics. Ultrasound has been widely used for diagnosis of cancer. It is relatively inexpensive and easy to use and, with ever-increasing improvements in image quality, it can have a diagnostic value comparable to MRI or CT imaging. Two dimensional (2D) ultrasound images of the target are compared to the corresponding CT projections conventionally used for radiotherapy planning. Similar to MRI, ultrasound imaging is benign and does not add extra undesirable radiation dose to the patient, and it is generally a non-invasive imaging modality. Ultrasound imaging is therefore a good candidate for organ motion monitoring between treatment fractions, which is a prerequisite for adaptive applications.

The initial use of ultrasound in radiotherapy followed the typical use of ultrasonic multiplanar reconstruction to visualize two perpendicular planes of the target. This first application of ultrasound was available only for prostate cancer treatment and showed many limitations, which have been documented in the literature. See Langen et al., "Evaluation of ultrasound-based prostate localization for image-guided radiotherapy," *Int. J. Radiat. Oncol. Biol. Physics*, vol. 57 (2003) at pp 635-44; and Van den Heuvel et al., "Independent verification of ultrasound based image-guided radiation treatment, using electronic portal imaging and implanted gold markers," *Med. Phys.*, vol. 30 (2003) at pp 2878-87. At the present time, only prostate cancer treatment has been clinically implemented using a mechanically swept transducer which continuously scans the target trans-perineally during irradiation. The position of the prostate is compared to the position of the prostate in a trans-perineal ultrasound image acquired prior to commencement of the procedure which is used for the therapy planning. During setup of the patient for each treatment fraction, ultrasound guidance determines the position of the targets and nearby organs at risk. The current position of the target can be used to recalculate dose and, if necessary, re-plan the patient treatment in adaptive applications. See Abramowitz et. al., "Noninvasive Real-time Prostate Tracking Using a Trans-perineal Ultrasound Approach", *In'l J. Rad., Oncol., Biol. & Physics*, vol.84 (2012) at pp S133, and Court et al., "Automatic online adaptive radiation therapy techniques for targets with significant shape change: a feasibility study," *Phys. Med. Biol.*, vol. 51 (2006) at pp 2493-50.

One of the problems inherent in the application of ultrasound for radiation therapy guidance is the need to maintain good acoustic coupling of the ultrasound probe to the body of the patient. Typical ultrasound probes have handles which are grasped by the clinician and used both to hold the probe and to press it into good acoustic contact with the skin of the patient. The problem this causes in radiotherapy is displacement of the tumor and adjacent and intervening tissues and organs by reason of the firm pressure needed to press the probe against the patient. Thus, the use of ultrasound itself becomes a source of re-positioning of the anatomy of the patient from that which is shown in the planning images, requiring treatment re-planning and reprogramming of the therapy delivery system as a result. Accordingly it is desirable to be able to use ultrasound for radiotherapy image guidance, but in a way which does not disrupt the constant positioning of organs and tissues necessary for a safe and effective radiotherapy procedure.

SUMMARY OF THE INVENTION

In accordance with the principles of the present invention, an ultrasonic diagnostic imaging system and imaging probe are described which are used for image guidance during radiotherapy without displacing the tissue and organ positioning observed during the therapy planning stage. The imaging probe is a thinly constructed matrix (two dimensional) array of piezoelectric transducers and control microbeamformer which are physically decoupled from other components of the conventional ultrasound probe. This thin, minimalistic probe construct enables the probe to be maintained in acoustic contact with the patient by means of medical grade adhesive tape or a belt, minimizing the amount of pressure needed to maintain the probe in acoustic contact with the patient and resultant tissue displacement problems. The use of a matrix array enables the imaging probe to be operated as a three dimensional phased array which can steer imaging beams over a volumetric region of the body including the therapy target region. Three dimensional imaging of the therapy site can thus be performed electronically (with no moving parts) in real time. The use of a belt or adhesive band to maintain the acoustic contact of the imaging probe with the patient obviates the need for an operator to hold the probe in the room with the radiation generating system and eliminates the need for complex or expensive probe retention devices such as robotic arm systems. Finally, the thin construct of the minimalistic probe reduces interference problems with the therapy beams.

DETAILED DESCRIPTION OF THE INVENTION

In radiotherapy, before, after, and possibly also during each treatment fraction, it is necessary to assess the treatment target position in the patient with respect to the position of the target used during preparation of the radiotherapy treatment plan. Presently, the alternatives proposed for holding the transducer in acoustic contact with the patient during scanning include human operators or robotic/mechanical arm systems. The major reason for this is the absence of probes specifically designed for radiotherapy applications. Conventional diagnostic imaging probes for external use are generally operated by a technician or physician, and have a case shaped with a handle which encloses the transducer crystals and the electronic components. But for ultrasound image guidance during a radiotherapy procedure the probe ideally must be operated remotely and work without the need for a human operator in the treatment room. The present invention comprises a probe specially designed for radiotherapy use in which the piezoelectric array elements and their microbeamformer are decoupled from other electronic components generally incorporated in an ultrasound probe, the piezoelectric elements are arrayed in a two dimensional matrix for real time electronic three dimensional imaging, the elements and microbeamformer are assembled in a flat and light case, and any other electronic parts are incorporated in the cable or, preferably, in the connector at the end of the probe cable. The active imaging elements of the probe therefore can be positioned on the patient and held in position using adhesive components or a belt.

Figure 1:
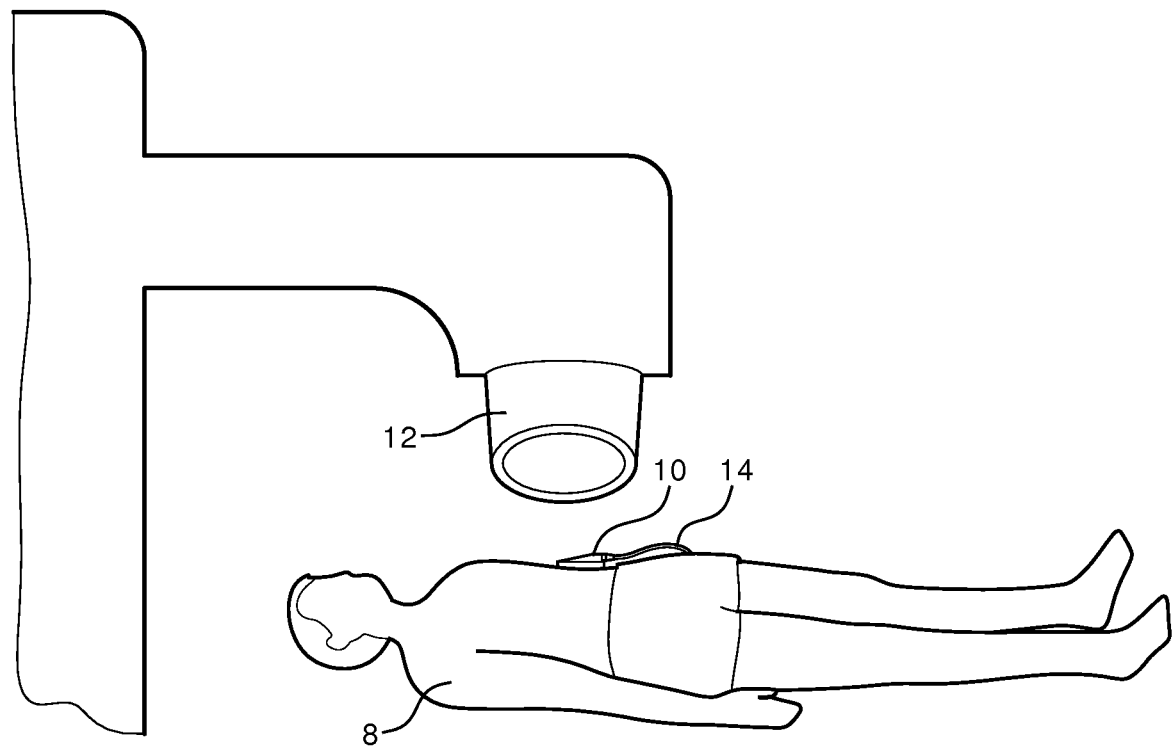
FIG. 1 illustrates a patient undergoing a radiotherapy procedure with a linear accelerator while the therapy target is visualized in real time by an ultrasonic imaging probe of the present invention.

Referring first to FIG. 1, a patient 8 is shown undergoing radiotherapy treatment. A linear accelerator 12 is positioned above the patient and delivers radiation beams in intervals called treatment fractions to target anatomy in the patient. In this example the therapeutic beams are directed at the liver of the patient for delivery of therapy to a liver tumor. Attached by adhesive tape or a belt to the abdomen of the patient is an ultrasonic imaging probe of the present invention. A probe cable 14 conveys imaging signals acquired by the probe to an ultrasonic imaging system such as that described in FIG. 2. The probe performs imaging of the tumor during the procedure so that a remote operator can observe any motion of the patient while therapy is being delivered. The probe also images the region of the tumor between treatment fractions so that the position of the tumor can be assessed in relation to the planning images before resuming treatment. It is seen that no operator is needed in the treatment room with the patient for the imaging probe and that the thin design of the probe poses little obstacle to the delivery of the radiation therapy.

Figure 2:
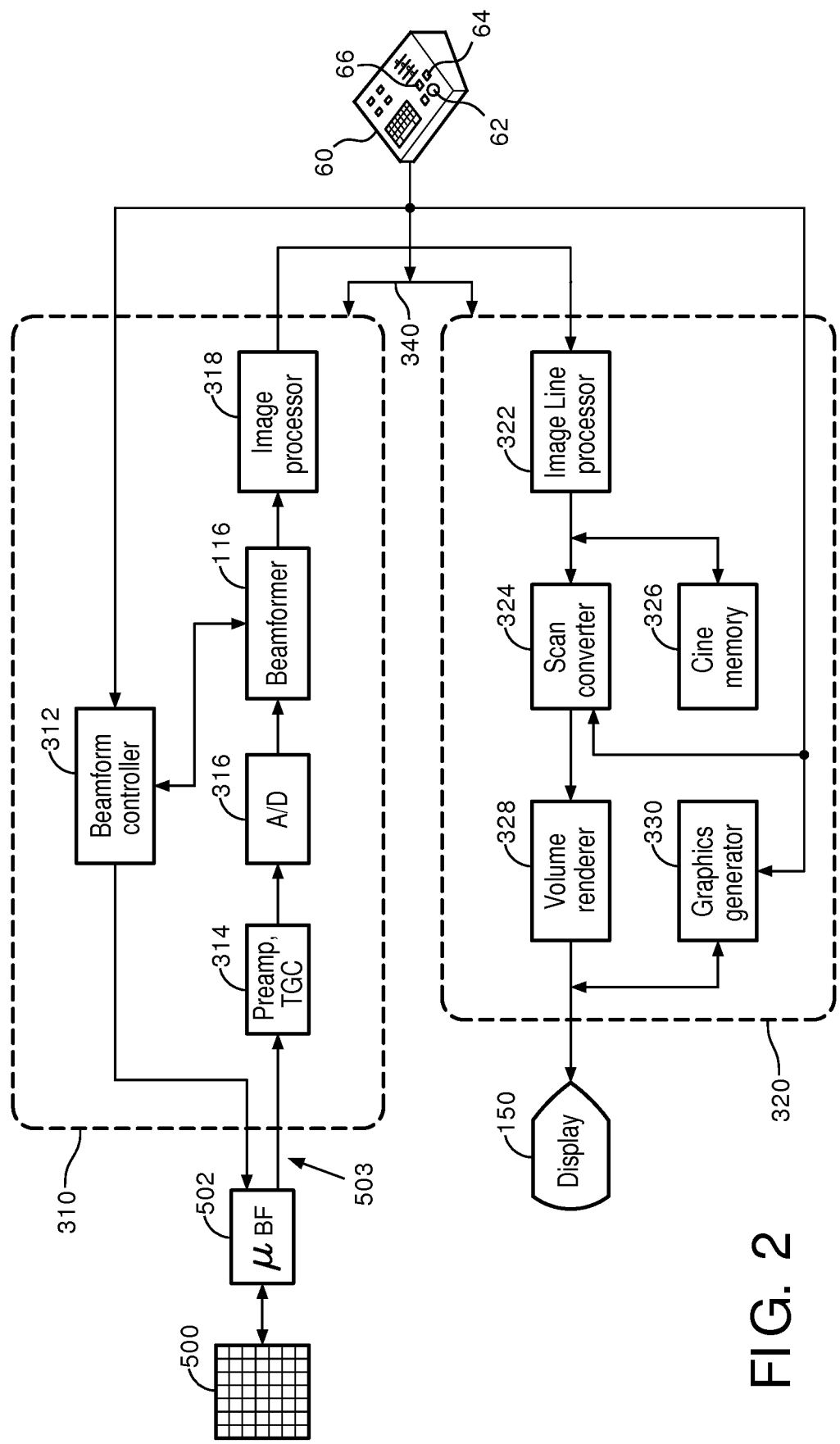
FIG. 2 illustrates an ultrasound imaging system suitable for use with an imaging probe of the present invention.

FIG. 2 illustrates in block diagram form an ultrasound system constructed in accordance with the principles of the present invention. In this implementation the probe 10 includes a two-dimensional array transducer 500 and a microbeamformer 502. The microbeamformer contains circuitry which control the signals applied to groups of elements ("patches") of the array transducer 500 and does some processing of the echo signals received by elements of each group to produce partially beamformed signals. Microbeamforming in the probe advantageously reduces the number of conductors in the cable 503 between the probe and the ultrasound system and is described in U.S. Pat. No. 5,997,479 (Savord et al.) and in U.S. Pat. No. 6,436,048 (Pesque). The probe 10 is coupled to the scanner subsystem 310 of the ultrasound system. The scanner includes a beamformer controller 312 which is responsive to a user control 60 and provides control signals to the microbeamformer 502 instructing the probe as to the timing, frequency, direction and focusing of transmit beams. The beamformer controller also controls the beamforming of received echo signals by its coupling to analog-to-digital (A/D) converters 316 and a beamformer 116. Echo signals received by the probe are amplified by preamplifier and TGC (time gain control) circuitry 314 in the scanner, then digitized by the A/D converters 316. The digitized echo signals are then formed into fully coherent beams by a beamformer 116. Optionally, signals from and to the elements of the array may be beamformed with the beamformer only. The echo signals are processed by an image processor 318 which performs digital filtering, B mode detection, and Doppler processing, and can also perform other signal processing such as harmonic separation, speckle reduction through frequency compounding, and other desired image processing.

The echo signals produced by the scanner subsystem 310 are coupled to the digital display subsystem 320, which processes the echo signals for display in the desired image format. The echo signals are processed by an image line processor 322, which is capable of sampling the echo signals, splicing segments of beams into complete line signals, and averaging line signals for signal-to-noise improvement or flow persistence. The image lines are scan converted into the desired image format by a scan converter 324 which performs R-theta conversion as is known in the art. The scan converter can also fill in image areas between received beams by interpolation. Individual images or image sequences are stored in a cine memory 326 during capture of image loops. The image in memory is also overlayed with graphics to be displayed with the image, which are generated by a graphics generator 330 which is responsive to the user control for the input of patient identifying information or the movement of cursors, for example.

For real-time volumetric imaging the display subsystem 320 also includes a volume renderer 328 which receives 3D data sets or sets of spatially separated 2D images and renders them into real-time three dimensional image. The 3D images of the scanned anatomy is displayed on a display 150. The user interface 60 includes controls 62-66 for control of the orientation of the volumetric region scanned by the two dimensional array probe. The user can select a function to be controlled by means of a control 66, such as the orientation of the region to be scanned. The user then uses a joystick or trackball 62 to position the scanned region. Once the scanned region has been set, the user depresses a control 64 to lock in the setting. The beamformer controller 312, the beamformer 116, and the microbeamformer 502 respond to these setting changes by transmitting beams in a desired direction by phased transmission with elements of the two dimensional array 500, then steering received beams in the same directions to acquire a series of receive beams throughout the volumetric region being scanned. These receive beams are processed into scan lines in 3D space, then rendered into a 3D image of the scanned volume by volume rendering. The volumetric region is thus repositioned and scanned with no moving elements in the probe. The effect of operation of these controls is illustrated in FIG. 4.

Figure 3:
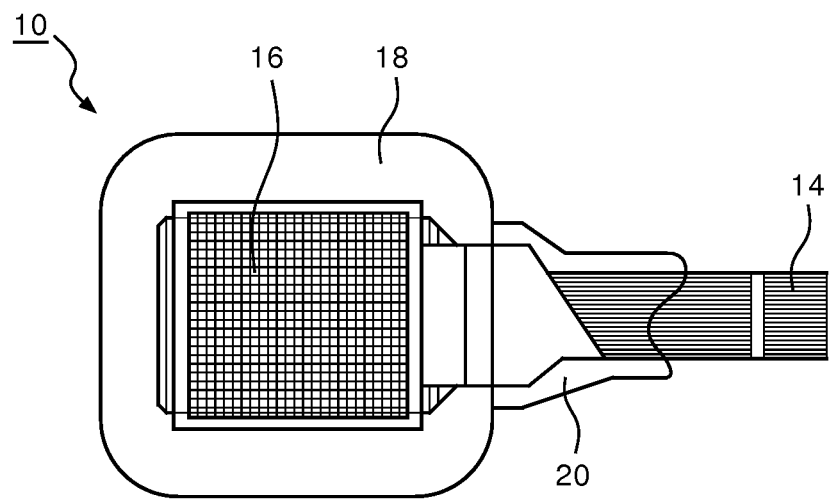
FIG. 3 is a bottom plan view of an imaging probe of the present invention.

FIG. 3 is a plan view of an imaging probe 10 of the present invention as viewed from the patient-contacting side. The probe includes a two dimensional (matrix) array 16 of piezoelectric transducer elements made, for example, of PZT ceramic. Piezoelectric elements are preferred in comparison to micromachined transducer elements (MUTs) by reason of their better acoustic transmit energy and sensitivity, which improves the performance of the probe in abdominal applications such as that shown in FIG. 1. The matrix array is backed by the microbeamformer application-specific integrated circuit which controls the operation of the elements of the array and produces partially beamformed signals from patches of elements of the matrix array to the ultrasound system over coaxial conductors of the cable 14. The conductors of the cable are coupled to connection pads of the microbeamformer integrated circuit. A cover seen in the side views of the probe covers the cable connections. The matrix array and microbeamformer assembly are mounted in a flat polymeric frame 18, giving the probe a low, substantially flat appearance. The probe will generally have a thickness or height (seen in FIGS. 1 and 4) which is less than either its width or length (seen in FIG. 3), enabling it to be securely taped or belted to the patient. There is an additional advantage of this thin probe, A strain relief 20 assists in and protects the attachment of the cable 14 to the main body and frame of the probe. The substantially flat construct of the probe, aided by its restricted number of components, enables the probe to be securely taped or belted to the skin of the patient and remain stationary throughout the radiotherapy procedure.

Other conventionally used materials, such as matching layers on the face of the transducer elements 16 and a covering layer (lens) are generally used on the face of the matrix array. A heat-dissipating element may be located on the back of the microbeamformer. Other electronic components such as impedance matching elements and preamplifiers for received signal are located in-line along the cable 14 or in the connector at the end of the cable by which the probe is plugged into the ultrasound system.

Figure 4:
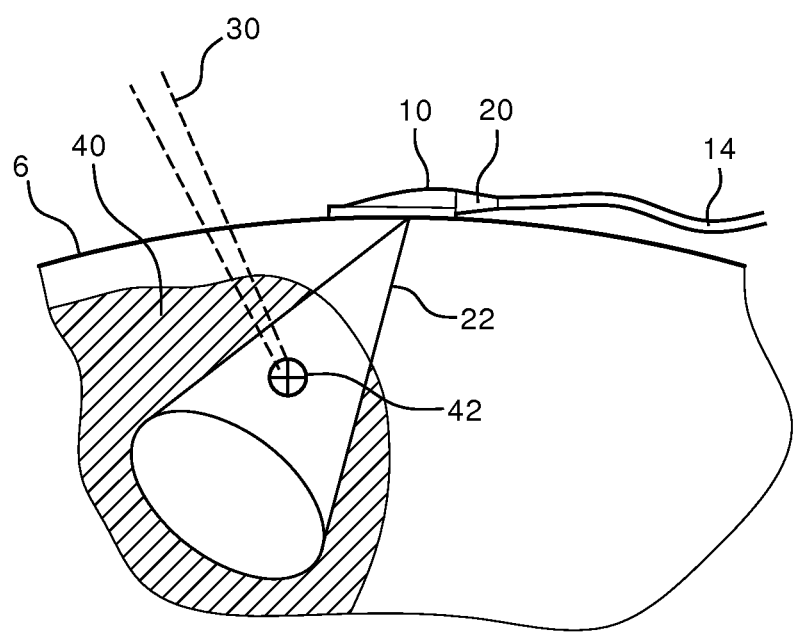
FIG. 4 illustrates 3D imaging of a tumor during radiotherapy with an imaging probe of the present invention.

FIG. 4 illustrates how the electronically steered imaging beams of an imaging probe 10 of the present invention enable the probe to be attached and used without impeding the delivery of therapeutic beams to the target region in the patient. This illustration shows a tumor 42 in the liver 40 of the patient. The imaging probe 10 is attached to the skin surface 6 of the patient and scans ultrasound beams in a conical pattern 22 for imaging. In this example it is seen that the imaging probe is not attached immediately above the target region, but adjacently to the side of it. The user controls 60 are manipulated to steer the conical scan region 22 at an angle so it encompasses the target region 42 to the side of the probe 10. This enables the therapeutic beams to be directed straight down into the patient's body, traveling a short or the shortest path through the body to reach the tumor 42. Thus, minimal healthy tissue is impacted by the therapy beam. It is seen that there is flexibility on where to direct the therapy beam; it can be repositioned to other entry points into the body and to the target region without interference from the probe. This enables the therapy beams 30 to be directed most effectively at the tumor, and to be positioned as needed to avoid damaging healthy organs and tissue around the therapy site. From this example additional advantages of the ultrasound probe constructed in accordance to the present invention become more evident. The two dimensional array enables the beam steering within regions adjacent to the probe and thin construct of the minimalistic (compact) probe reduces interference with the therapy beams. This increases flexibility in the therapy planning procedures, such that the therapeutic beams path can be reduced and brought to the close proximity of the probe without causing an interference with electronic components of the probe.

The invention claimed is:

1. An ultrasonic diagnostic imaging system for imaging a patient undergoing radiotherapy treatment, the ultrasonic diagnostic imaging system comprising:
    an ultrasound probe comprising:
        a two dimensional array transducer, the ultrasound probe having a patient-contacting face with a width dimension and a length dimension, wherein a thickness of the ultrasound probe normal to the patient-contacting face is less than both the width and length dimensions;
        a microbeamformer application-specific integrated circuit coupled to a face of the array transducer opposite the patient-contacting face; and
        a probe cable coupled to the microbeamformer at a first end and comprising a connector at a second end opposite the first end, wherein the connector comprises at least one of an impedance matching element or a preamplifier element,
        wherein the ultrasound probe is adapted to electronically steer ultrasound beams in a volumetric region comprising a target region;
    an ultrasound system, remotely located from the ultrasound probe, and connected to the ultrasound probe by the connector at the second end of the probe cable, the ultrasound system adapted to process ultrasound signals produced by the ultrasound probe for the production of three dimensional images of the target region of a patient; and
    a belt or adhesive band which enables attachment of the ultrasound probe to the patient with the patient-contacting face acoustically coupled to the patient for securing the ultrasound probe to the patient while the patient undergoes radiotherapy treatment and the ultrasound system produces images of the target region either during treatment or between treatment fractions.

2. The ultrasonic diagnostic imaging system of claim 1, wherein the ultrasound probe further comprises a polymeric frame supporting the array transducer, the microbeamformer, and the probe cable, and wherein the thickness of the probe corresponds to a height of the polymeric frame above the patient when the probe is attached to the patient.

3. The ultrasonic diagnostic imaging system of claim 1, wherein the ultrasound system further comprises a volume renderer adapted to produce the three dimensional images of the target region.

4. The ultrasonic diagnostic imaging system of claim 1, wherein the ultrasound system further comprises a user control which is operable to orient the volumetric region scanned by the ultrasound probe with respect to the ultrasound array.

5. The ultrasonic diagnostic imaging system of claim 4, wherein the user control is operated to orient the volumetric region to be oriented to scan a target region which is located laterally to the side of the ultrasound probe.

6. A method for ultrasonically imaging a patient undergoing radiotherapy treatment, the method comprising:
   attaching to the patient an ultrasound probe comprising a two dimensional array transducer, a microbeamformer application-specific integrated circuit coupled to the array transducer, a probe cable coupled to the microbeamformer at a first end and comprising a connector at a second end opposite the first end, wherein the connector comprises at least one of an impedance matching element or a preamplifier element, and wherein the ultrasound probe has a patient-contacting face with a width dimension and a length dimension, and wherein a thickness of the ultrasound probe normal to the patient-contacting face is less than both the width and length dimensions;
   conducting radiotherapy on a target region of the patient;
   steering ultrasound beams in a volumetric region comprising the target region by providing control signals to the microbeamformer application-specific integrated circuit from a beamformer controller of an ultrasound system remote from the ultrasound probe and coupled to the ultrasound probe by the connector of the probe cable;
   producing, by the ultrasound system, three dimensional ultrasound images of the target region from signals produced by the ultrasound probe; and
   adjusting the radiotherapy based upon the three dimensional ultrasound images.

7. The method of claim 6, wherein attaching further comprises:
   attaching the ultrasound probe to the patient with a belt or adhesive band that secures the ultrasound probe to the patient with the patient-contacting face acoustically coupled to the patient.

8. The method of claim 6, further comprising:
   scanning the volumetric region to produce therapy planning images; and
   planning radiotherapy using the therapy planning images.

9. The method of claim 8, wherein the attaching the ultrasound probe to the patient comprises attaching the ultrasound probe such that the target region is not underneath the ultrasound probe.

10. The method of claim 9, wherein the ultrasound system further comprises a user control coupled to the ultrasound system, the method further comprising adjusting the user control to visualize a target region which is not beneath the ultrasound probe.

11. The method of claim 6, wherein the producing three dimensional ultrasound images comprises producing three dimensional ultrasound images of the target region between treatment fractions of a treatment plan; and
   wherein adjusting the radiotherapy further comprises adjusting the radiotherapy based upon the three dimensional ultrasound images of the target region produced between treatment fractions.

* * * * *